(12) United States Patent
San et al.

(10) Patent No.: US 8,709,753 B2
(45) Date of Patent: Apr. 29, 2014

(54) NATIVE NAD-DEPENDENT GAPDH REPLACED WITH NADP-DEPENDENT GAPDH PLUS NADK

(71) Applicant: William Marsh Rice University, Houston, TX (US)

(72) Inventors: Ka-Yiu San, Houston, TX (US); George N. Bennett, Houston, TX (US); Yipeng Wang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 13/680,608

(22) Filed: Nov. 19, 2012

(65) Prior Publication Data

US 2013/0084600 A1 Apr. 4, 2013

Related U.S. Application Data

(63) Continuation of application No. PCT/US2011/038619, filed on May 31, 2011.

(60) Provisional application No. 61/350,382, filed on Jun. 1, 2010.

(51) Int. Cl.
C12N 15/70 (2006.01)

(52) U.S. Cl.
USPC ..................................... 435/52; 435/252.33

(58) Field of Classification Search
USPC .................................................. 435/252.3, 77
See application file for complete search history.

(56) References Cited

FOREIGN PATENT DOCUMENTS

| WO | 2008028002 | 6/2008 |
|----|------------|--------|
| WO | PCT/US2011/038619 | 6/2008 |

OTHER PUBLICATIONS

Li et al., 2009. Overexpression of NAD kinase in recombinant *Escherichia coli* harboring the phbCAB operon improves Poly (3-hydroxybutyrate) production. Appl. Microbiol. Biotechnol. 83: 939-947.*
Burgess et al., Possible dissociation of the heparin-binding. Journal of Cell Biology, vol. 111, 2129-2138, 1990.*
Lin et al., Structure-Function Relationship. Biochemistry, vol. 14, 1559-1563, 1975.*
Fillinger, S., et al., "Two glyceraldehyde-3-phosphate dehydrogenases with opposite physiological roles in a nonphotosynthetic bacterium." J Biol Chem, 2000. 275(19): p. 14031-7.
Kawai, S., et al., "Molecular characterization of *Escherichia coli* NAD kinase." Eur J Biochem, 2001. 268(15): p. 4359-65.
Walton, A.Z. and J.D. Stewart, "Understanding and improving NADPH-dependent reactions by nongrowing *Escherichia coli* cells." Biotechnol Prog, 2004. 20(2): p. 403-11.
Alper H., et al., "Identifying gene targets for the metabolic engineering of lycopene biosynthesis in *Escherichia coli*." Metab Eng, 2005. 7(3): p. 155-64.
Kurata, A., et al., "2-Haloacrylate reductase, a novel enzyme of the medium chain dehydrogenase/reductase superfamily that catalyzes the reduction of a carbon-carbon double bond of unsaturated organohalogen compounds." J Biol Chem, 2005. 280(21): p. 20286-91.
Phillips, G.J., S.K. Park, and D. Huber, "High copy number plasmids compatible with commonly used cloning vectors." Biotechniques, 2000. 28(3): p. 400-2, 404, 406 passim.
Ganter, C. and A. Pluckthun, "Glycine to alanine substitutions in helices of glyceraldehyde-3-phosphate dehydrogenase: effects on stability." Biochemistry, 1990. 29(40): p. 9395-402.
Martínez I, Zhu J, Lin H, Bennett GN, San KY, "Replacing *Escherichia coli* NAD-dependent glyceraldehyde 3phosphate dehydrogenase (GAPDH) with a NADP-dependent enzyme from *Clostridium acetobutylicum* facilitates Nadph dependent pathways," Metab Eng. Nov. 2008;10(6):352-9. Epub Sep. 23, 2008.

* cited by examiner

*Primary Examiner* — Anand Desai
*Assistant Examiner* — Rama P Ramanujam
(74) *Attorney, Agent, or Firm* — Boulware & Valoir

(57) ABSTRACT

This invention is metabolically engineer bacterial strains that provide increased intracellular NADPH availability for the purpose of increasing the yield and productivity of NADPH-dependent compounds. In the invention, native NAD-dependent GAPDH is replaced with NADP-dependent GAPDH plus overexpressed NADK. Uses for the bacteria are also provided.

9 Claims, 3 Drawing Sheets

NATIVE NAD-DEPENDENT GAPDH REPLACED WITH NADP-DEPENDENT GAPDH PLUS NADK

CROSS-REFERENCE TO RELATED APPLICATIONS

Figure 1:
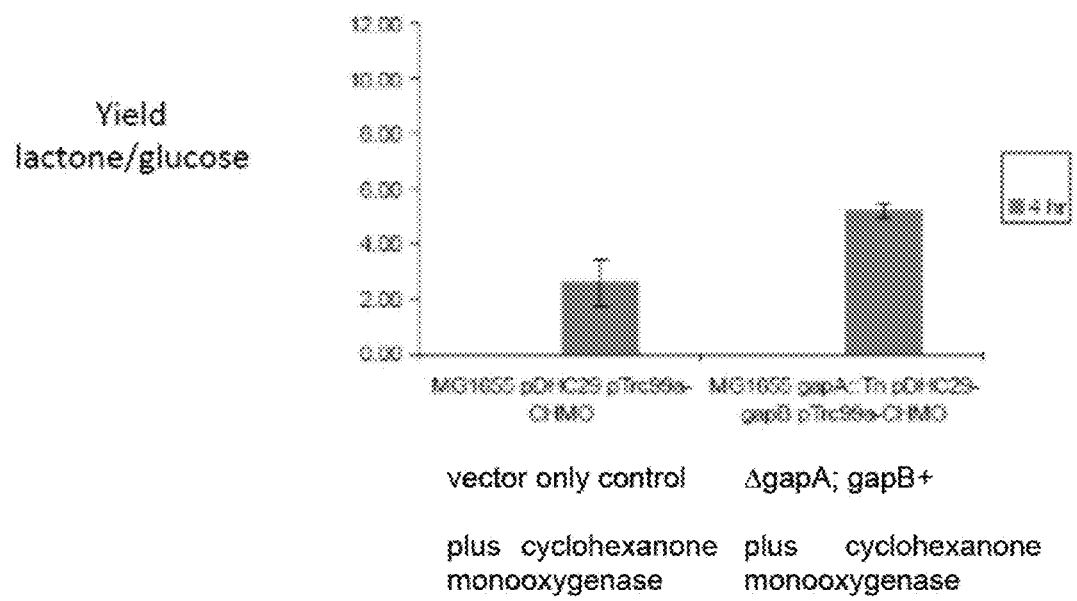

This application is a continuation of International Application Number PCT/US11/38619, filed May 31, 2011, which claims priority to U.S. Ser. No. 61/350,382, filed Jun. 1, 2010. Both applications are incorporated by reference in their entirety.

STATEMENT REGARDING FEDERALLY SPONSORED RESEARCH OR DEVELOPMENT

This invention was made with government support under Grant No. CBET-0828516 awarded by the National Science Foundation. The government has certain rights in the invention.

REFERENCE TO A COMPACT DISK APPENDIX

Not applicable.

FIELD OF THE INVENTION

This invention relates to metabolically engineered bacterial strains that provide greatly increased intracellular NADPH levels for the purpose of increasing the yield and productivity of NADPH-dependent compounds.

BACKGROUND OF THE INVENTION

Nicotinamide adenine dinucleotide (NAD) and its relative nicotinamide adenine dinucleotide phosphate (NADP) are two of the most important coenzymes in the cell. NADP is simply NAD with a third phosphate group attached as shown:

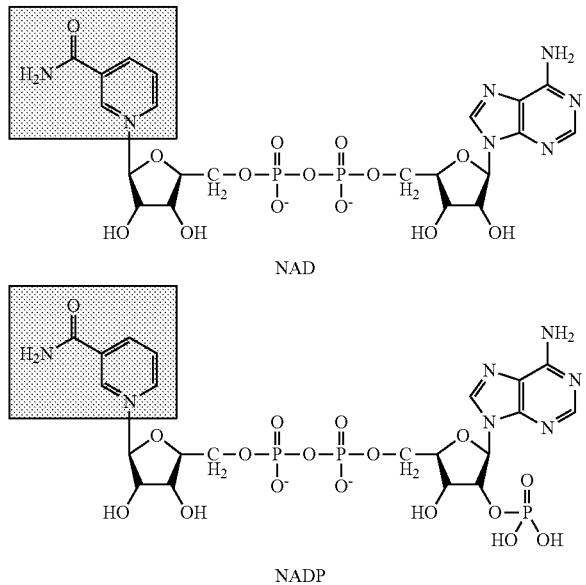

NAD

NADP

Because of the positive charge on the nitrogen atom in the nicotinamide ring (box), the oxidized forms of these important redox reagents are often depicted as NAD+ and NADP+ respectively.

In cells, most oxidations are accomplished by the removal of hydrogen atoms. Both of these coenzymes play crucial roles in this. Each molecule of NAD+ (or NADP+) can acquire two electrons; that is, be reduced by two electrons. However, only one proton accompanies the reduction. The other is liberated into the surrounding medium. For NAD, the reaction is thus:

$$NAD^+ + 2H \rightarrow NADH + H^+$$

NAD participates in many redox reactions in cells, including those in glycolysis and most of those in the citric acid cycle of cellular respiration.

NADP is the reducing agent produced by the light reactions of photosynthesis, consumed in the Calvin cycle of photosynthesis and used in many other anabolic reactions in both plants and animals. Because NADP is used in anabolic reactions, it is desired to increase its levels in order to drive bacteria towards the synthesis of desired compounds.

The purpose of this invention is to manipulate the *E. coli* intracellular NADPH availability, which in turn increases the yield and productivity of NADPH-dependent synthesis of compounds, such as the biodegradable polymer poly-3-hydroxybutyrate (PHB), sorbitol, alcohols, amino acids, lycopene terpenoids, flavanoids, carotenoids, mevalonate, purines, pyramidines, antibiotics, cholesterol, steroids, and the like. NADP dependent compounds include fatty acids of varying chain lengths, or lycopene, which can be used as an antioxidant or precursor to produce other carotenoids. Increased NADP levels can also be useful for recycling some enzymes such as P450s, some of which require NADPH, and these can be active in drug metabolism and specialized oxidations. Additionally, chiral alcohols are products that often require reduction using NADPH. Thus, increasing NADP levels can be useful in a great many different contexts and applications.

SUMMARY OF THE INVENTION

We have developed a novel system to increase in vivo NADPH availability through genetic engineering. The system consists of two parts.

First, we replaced a native NAD-dependent D-glyceraldehyde-3-phosphate dehydrogenase (GAPDH) gene, gapA, in *E. coli* with an NADP-dependent GAPDH gene, gapB, from *Bacillus subtilis* [1]. The gapB enzyme catalyzes the following reaction:

D-glyceraldehyde-3-phosphate+phosphate+
NADP$^+$→1,3-diphosphateglycerate+NADPH

This approach provides an efficient source of NADPH, because for every mole of glucose passing through the glycolysis pathway, two moles of NADPH will be formed. This is in sharp contrast to the native system where NADH will be formed.

Efficient as it is to convert NADP+ into NADPH, this approach is nonetheless limited by the low bioavailability of NADP+ inside the cell. To solve this problem, in the second part of the invention, we co-expressed gapB with an *E. coli* NAD kinase, encoded by nadK, which is an enzyme that converts NAD to NADP [2], providing an improved source of NADP for gapB. With both added components, cofactor availability and/or flux is greatly improved.

Thus, the invention generally relates to bacteria where native NAD dependant GAPDH is replaced with a NADP dependant GAPDH, and wherein an NAD kinase is overexpressed, and methods of using such bacteria to make various NADP dependant products.

As used herein "recombinant" is relating to, derived from, or containing genetically engineered material. In other words, the genome was intentionally manipulated in some way.

"Overexpression" or "overexpressed" is defined herein to be at least 150% of protein activity as compared with an appropriate control species. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. In a preferred embodiment, one or more expression vectors encoding the required protein(s) is/are added to the cell.

The terms "disruption" as used herein, refer to cell strains in which the native gene or promoter is mutated, deleted, interrupted, or down regulated in such a way as to decrease the activity of the gene at least 90% over the wild type undisrupted gene. A gene can be completely (100%) reduced by knockout or removal of the entire genomic DNA sequence. Use of a frame shift mutation, early stop codon, point mutations of critical residues, or deletions or insertions, and the like, can completely inactivate (100%) gene product by completely preventing transcription and/or translation of active protein.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| | |
|---|---|
| CAA43 | 2-haloacrylate dehydrogenase |
| CHMO | Cyclohexanone monooxygenase |
| EDTA | Ethylenediaminetetraacetic acid |
| GAPDH | D-glyceraldehyde-3-phosphate dehydrogenase |
| NAD | Nicotinamide adenine dinucleotide |
| NADK | NAD kinase |
| NADP | Nicotinamide adenine dinucleotide phosphate |
| PHB | Poly-3-hydroxybutyrate |

We have exemplified this system using *E. coli* and genes from *Bacillus subtilis* and *E. coli*. However, this was for convenience only because these genes were already available, and the invention can be used with any bacteria, since all bacteria have these enzymes and/or their equivalent. In fact, many such genes are already available in GenBank and other databases and can readily be employed herein. Enteric bacteria such as *E. coli* and others may be preferred in some circumstances due to familiarity with large-scale culture of such bacteria.

DETAILED DESCRIPTION OF THE FIGURES

FIG. 1: Overexpression of gapB increases cyclohexanone monooxygenase (CHMO) consumption of cyclohexnone, which requires NADPH as cofactor. Plasmid pTrc99a is modified to include CHMO, and placed into the ΔgapA, gapB+ bacteria.

Figure 2:
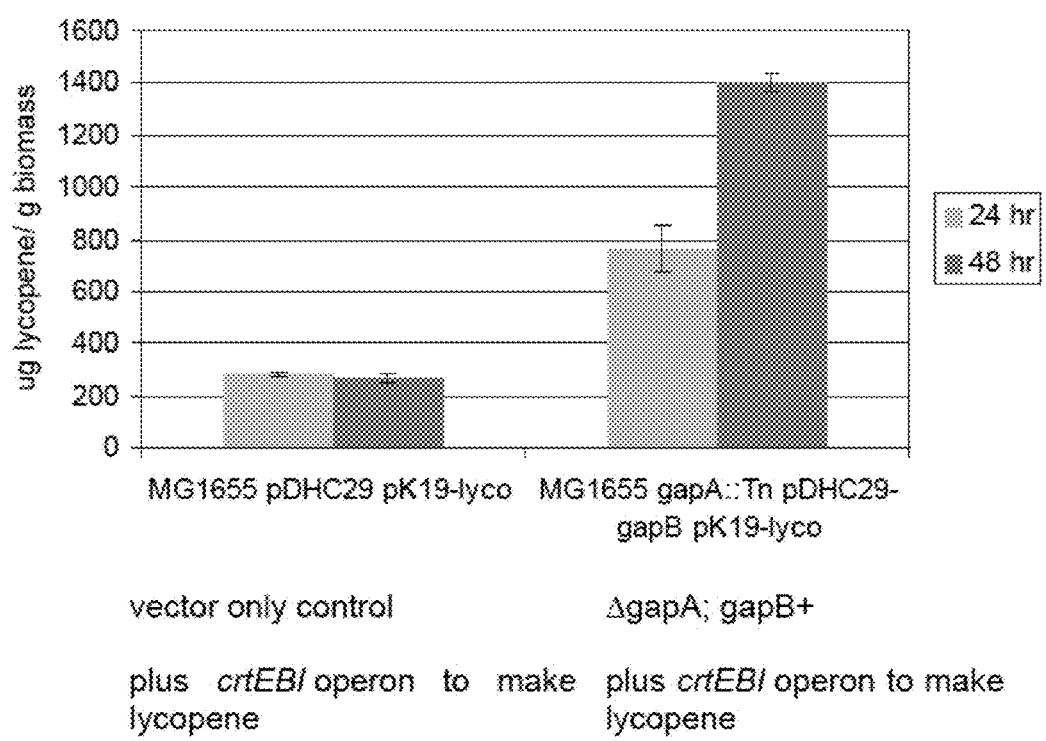

FIG. 2: Overexpression of gapB increases lycopene production, which requires a large amount of NADPH as cofactor (16 mole of NADPH for 1 mole of lycopene). pK19-lyco is a plasmid encoding the crtEBI operon, which is the lycopene biosynthesis operon from *Erwinia herbicola*.

Figure 3:
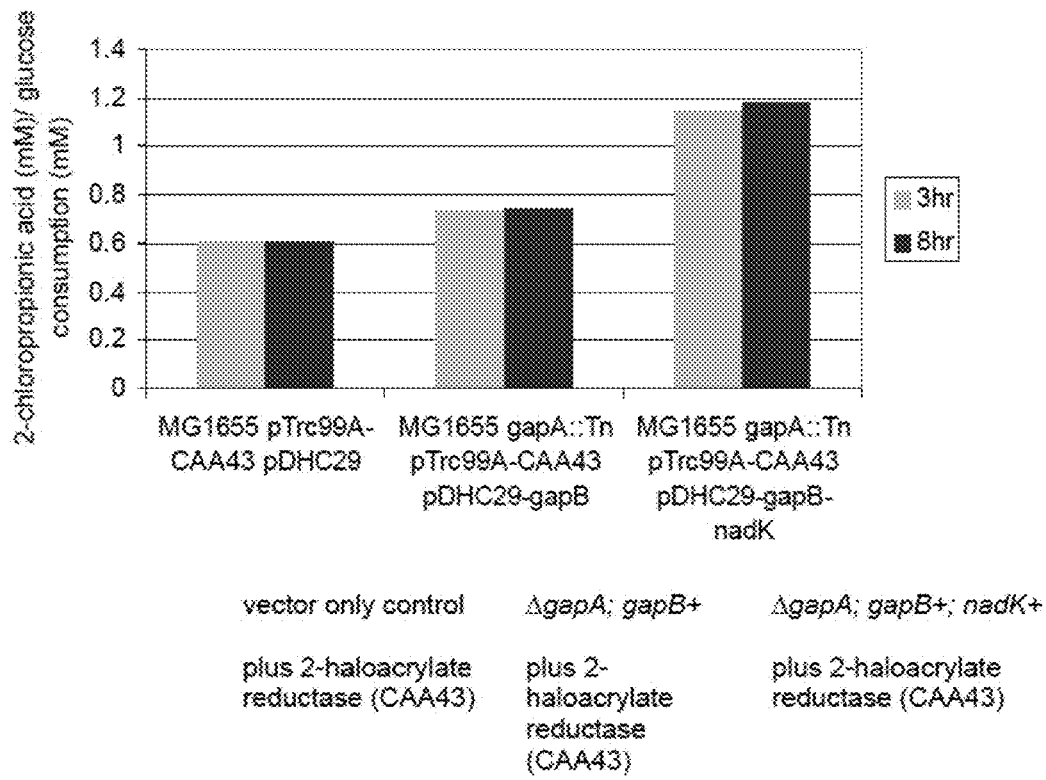

FIG. 3: Overexpression of both gapB and NAD kinase increases yield of 2-chloropropionic acid formed by oxidization of 2-chloroacrylate by 2-haloacrylate dehydrogenase (CAA43) even more than just overexpression of gapB. pTrc99a-CAA43 is a plasmid encoding 2-haloacrylate dehydrogenase.

DETAILED DESCRIPTION OF THE INVENTION

Exemplary genes/proteins that can be used in the invention are listed below in Table 1, wherein the gene/protein actually used is indicated in bold. The table is by no means complete, but searching the databases with the relevant protein sequences will identify the relevant proteins in a large number of bacterial species. Alternatively, one can search by protein name. Each protein sequence is connected to a gene sequence, which can be used to generate either expression vectors or knockout vectors, etc., which can be used to manipulate the bacteria according to the claimed invention. As is apparent from Table 1, the proteins in question are remarkably conserved in a variety of species, thus the method is predicated to be usable in a great many species. In some species, there may be more than one gene that needs to be disrupted for optimal performance, although in most cases a single gene disruption should suffice.

TABLE 1

Exemplary genes/proteins for use in the invention

| Species | Gene | Protein | % Identity | Acc. No. |
|---|---|---|---|---|
| E. coli | gapA | glyceraldehyde-3-phosphate dehydrogenase A aka GAPDH, NAD-dependant | 100% | NC_000913 |
| Shigella flexneri | gapA | GAPDH | 99% | YP_688934.1 |
| Salmonella enterica | gapA | GAPDH | 99% | NP_456222.1 |
| Citrobacter rodentium | gapA | GAPDH | 97% | YP_003364860.1 |
| Klebsiella pneumoniae | gapA | GAPDH | 96% | YP_002918985.1 |

TABLE 1-continued

Exemplary genes/proteins for use in the invention

| Species | Gene | Protein | % Identity | Acc. No. |
|---|---|---|---|---|
| Providencia rettgeri | gapA | GAPDH | 91% | ZP_06123668.1 |
| Erwinia amylovora | gapA | GAPDH | 89% | YP_003531334.1 |
| Bacillus subtilus | gapB | Glyceraldehyde-3-phosphate dehydrogenase 2 aka GAPDH, NADP dependant | 100% | AAC00355 |
| Bacillus amyloliquefaciens | gapB | GAPDH | 88% | YP_001422195.1 |
| Bacillus thuringiensis | gap1 | GAPDH | 74% | YP_002448147.1| |
| Macrococcus caseolyticus | gapB | GAPDH | 69% | YP_002560757.1 |
| Exiguobacterium sibiricum | Exig_2199 | GAPDH | 66% | YP_001814668. |
| Costridium acetobutylicum | gapC | GAPDH | 48% | ADZ19759 |
| Clostridium botulinum | gap | GADPH | 63% | YP_001786486.1 |
| E. coli | nadK | NAD Kinase (NADK) | 100 | AAC75664 |
| Citrobacter sp. 30_2 | CSAG_02408 | NADK | 99% | ZP_04560011.1 |
| Enterobacter cloacae | Entcl_110 | NADK or Acox kinase | 97% | YP_003940658.1| |
| Salmonella enterica | ppnK | NADK | 96% | ZP_02347266.1 |
| Cronobacter turicensis | ppnk | NADK | 91% | YP_003211564.1 |

Example 1

The gapB gene was PCR amplified from *Bacillus subtilis* 168 genomic DNA and cloned into vector pDHC29 under the Plac promoter [6]. NADP+ dependent GAPDH activity of gapB was confirmed by spectrophotometrical analysis based on measurement of NADPH at OD 340 nm. The reaction mixture included 40 mM Triethanolamine, 50 mM Sodium biphosphate, 0.2 mM ethylenediaminetetraacetic acid (EDTA), 1 mM NADP+, 1 mM Glyceraldehyde-3-phosphate and whole cell lysate. gapB showed higher activity in the presence of NADP than NAD, while the wild type control MG1655 pDHC29 preferred NAD over NADP (Table 2).

TABLE 2

NAD$^+$- or NADP$^+$-dependent GAPDH activity

| | NAD$^+$ (IU*/mg protein) | NADP$^+$ (IU*/mg protein) |
|---|---|---|
| MG1655 pDHC29 (control) | 461 | 18 |
| MG1655 gapA::Tn pDHC29-gapB (ΔgapA, gapB+) | 90 | 314 |

*One IU of GAPDH activity is the amount of enzyme required to convert 1 μmol of substrate per min at 37° C.

To replace native *E. coli* GAPDH gene, gapA, with gapB, pDHC29-gapB was transformed in a gapA null mutant MG1655 gapA::Tn, which has a transposon insertion in P1 promoter region of gapA and lost gapA activity [7]. This recombinant strain was later introduced with pTrc99a-CHMO, pK19-lyco or pTrc99a-CAA43 to test NADPH availability.

We have found that overexpression of NADP$^+$-dependent gapB, or both gapB and NADK, greatly increased NADPH availability in the cell, which in turn resulted in higher yield of NADPH dependent compounds. The level of cofactor can go up 10, 20 or more fold over the pre-modified bacteria.

To validate this novel system, the resulting recombinant *E. coli* strains were tested in reporting systems that produce NADPH-dependent compounds.

The first reporting system was the cyclohexanone monooxygenase (CHMO) from *Acinetobacter* sp. NCIB 9871. CHMO catalyzes Baeyer-Villiger (BV) reactions and oxidizes cyclohexanones into δ- and ε-caprolactones with high enantioselectivity (>95%) using NADPH as cofactor, and thereby gives a direct measurement of NADPH availability in the cell under aerobic conditions [3].

cyclohexanone → hexano-6-lactone
(O$_2$ + NADPH + H$^+$ → H$_2$O + NADP$^+$)

The second reporting system we used involved production of lycopene under aerobic conditions. Lycopene has been produced in *E. coli* using crtEBI operon from *Erwinia herbicola* [4] containing genes crtE, crtB, and crtI, together with certain native genes. 16 moles of NADPH are required to produce 1 mole of lycopene.

The third reporting system we have developed is an anaerobic system which utilizes the 2-haloacrylate reductase CAA43 from soil bacterium *Burkholderia* sp. WS. This enzyme reduces 2-chloroacrylate to 2-chloropropionic acid while oxidizing NADPH to NADP+ [5].

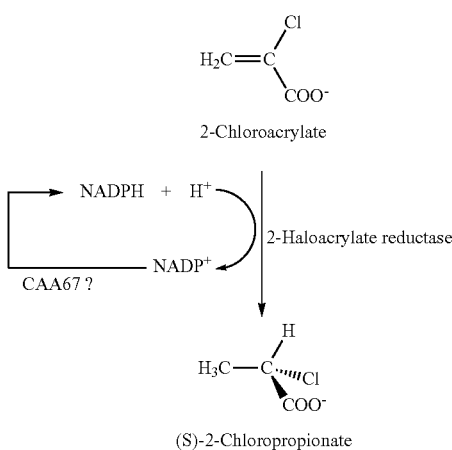

(S)-2-Chloropropionate

In the monooxygenase assay, we found that overexpression of gapB greatly increased consumption of cyclohexonone per mole of glucose used, indicating that in the presence of gapB, glucose generates more NADPH to be utilized in cyclohexonone oxidization (FIG. 1).

Similarly in the lycopene assay, the gapB+ recombinant strain showed higher lycopene production than wild type strain with vector control (FIG. 2).

When both gapB and NAD kinase were overexpressed, the recombinant strain showed a higher yield of 2-chloropropionic acid, which was reduced from 2-chloroacrylate by 2-haloacrylate dehydrogenase using NADPH as cofactor (FIG. 3). The yield was further improved over just the overexpression of gapB alone.

In summary, this invention established an in vivo system to increase NADPH availability in *E. coli*. By replacing its native NAD+-dependent gapA with NADP+-dependent gapB from *B. subtilis*, we were able to produce NADPH dependent compounds in *E. coli* in a higher yield. The increase was even more pronounced when NAD kinase was co-expressed along with gapB.

Example 2

In addition to the bacteria described above, we also replaced *E. coli* NAD-dependent glyceraldehyde 3-phosphate dehydrogenase (GAPDH) with a NADP-dependent enzyme from *Clostridium acetobutylicum* [8]. We constructed a recombinant *E. coli* strain by replacing the native NAD-dependent gapA gene with a NADP-dependent GAPDH from *Clostridium acetobutylicum*, encoded by the gene gapC. The recombinant strain produces 2 moles of NADPH, instead of NADH, per mole of glucose consumed.

The effectiveness of the NADPH enhancing system was again tested using the production of lycopene and ε-caprolactone as model systems using two different background strains. The recombinant strains, with increased NADPH availability, consistently showed significant higher productivity than the parent strains.

The NADK overexpression vector from above will be added to the base ΔgapA/gapC+ strain, and is predicted to further improve the base strain in a manner similar to that already shown in the original experiments (FIG. 3).

Example 3

NADP and NADPH are used in a great many anabolic reactions, which are too numerous to be listed herein. However, a listing of NADP dependent enzymes can be found at en.wikipedia.org/wiki/Category:NADPH-dependent_enzymes (incorporated herein by reference). Of the hundreds of enzymes listed herein, some of the more important include limonene monooxygenases, hydroxybenzoate monooxygenases, steroid reductases, 6-methylsalicylic-acid synthase, acetoacetyl-CoA reductase, acyl-CoA dehydrogenase, alcohol dehydrogenases, aldehyde dehydrogenases, alkene monooxygenase, coA-glutathione reductase, D-lysopine dehydrogenase, D-nopaline dehydrogenase, estradiol dehydrogenases, farnesol dehydrogenase, fatty-acid synthase, formate dehydrogenase, formyltetrahydrofolate dehydrogenase, lovastatin nonaketide synthase, salicylate 1-monooxygenase, and taxane hydroxylases. Thus, it is apparent that the bacteria of the invention can be used in a great many biosynthetic applications.

The following references are incorporated by reference herein in their entirety.

1. Fillinger, S., et al., "Two glyceraldehyde-3-phosphate dehydrogenases with opposite physiological roles in a non-photosynthetic bacterium." *J Biol Chem*, 2000. 275(19): p. 14031-7.
2. Kawai, S., et al., "Molecular characterization of *Escherichia coli* NAD kinase." *Eur J Biochem*, 2001. 268(15): p. 4359-65.
3. Walton, A. Z. and J. D. Stewart, "Understanding and improving NADPH-dependent reactions by nongrowing *Escherichia coli* cells." *Biotechnol Prog*, 2004. 20(2): p. 403-11.
4. Alper, H., et al., "Identifying gene targets for the metabolic engineering of lycopene biosynthesis in *Escherichia coli*." *Metab Eng*, 2005. 7(3): p. 155-64.
5. Kurata, A., et al., "2-Haloacrylate reductase, a novel enzyme of the medium chain dehydrogenase/reductase superfamily that catalyzes the reduction of a carbon-carbon double bond of unsaturated organohalogen compounds." *J Biol Chem*, 2005. 280(21): p. 20286-91.
6. Phillips, G. J., S. K. Park, and D. Huber, "High copy number plasmids compatible with commonly used cloning vectors." *Biotechniques*, 2000. 28(3): p. 400-2, 404, 406 passim.
7. Ganter, C. and A. Pluckthun, "Glycine to alanine substitutions in helices of glyceraldehyde-3-phosphate dehydrogenase: effects on stability." *Biochemistry*, 1990. 29(40): p. 9395-402.
8. Martínez I, Zhu J, Lin H, Bennett G N, San K Y, "Replacing *Escherichia coli* NAD-dependent glyceraldehyde 3-phosphate dehydrogenase (GAPDH) with a NADP-dependent enzyme from *Clostridium acetobutylicum* facilitates NADPH dependent pathways," *Metab Eng.* 2008 November; 10(6):352-9. Epub 2008 Sep. 23.

We claim:

1. A recombinant bacteria comprising i) a disrupted native NAD-dependent D-glyceraldehyde-3-phosphate dehydrogenase (GAPDH), ii) an overexpressed NADP-dependent GAPDH, and iii) an overexpressed NAD kinase, wherein said bacteria has a disrupted gapA gene, plus an overexpressed gapB or gapC gene, and an overexpressed nadK gene.

2. The recombinant bacteria of claim 1, comprising a deleted native gapA gene, plus one or more expression vectors comprising an overexpressed gene encoding NADP-dependent GAPDH and an overexpressed gene encoding a NAD kinase.

3. The recombinant bacteria of claim 1 that produces 10 fold more NADPH than said bacteria without i), ii), and iii).

4. The recombinant bacteria of claim 1 that produces 20 fold more NADPH than said bacteria without i), ii), and iii).

5. A recombinant *E. coli*, comprising i) a deleted native gapA gene, plus one or more expression vectors comprising ii) an overexpressed NADP-dependent GAPDH, and iii) an overexpressed NAD kinase.

6. The recombinant *E. coli* of claim 5, that produces 10 fold more NADPH than said bacteria without i), ii), and iii).

7. The recombinant *E. coli* of claim 5, that produces 20 fold more NADPH than said bacteria without i), ii), and iii).

8. A method of making a product that requires NADP in its synthesis, comprising culturing the bacteria of any one of claims 1-7 in a culture media under conditions sufficient to make a product that requires NADP cofactor in its biosynthesis, and isolating said product from the culture media, or said bacteria, or both, wherein said product is selected from the group consisting of amino acids, alcohols, fatty acids, poly-3-hydroxybutyrate, sorbitol, lycopene, flavanoids, carotenoids, mevalonate, glutamate, purines, pyrimidines, antibiotics, cholesterol, and steroids.

9. The recombinant *E. coli* of claim 4, comprising a disrupted gapA gene, plus an overexpressed gapB or gapC gene, plus an overexpressed nadK gene.

* * * * *